(12) United States Patent
Divi et al.

(10) Patent No.: US 8,148,527 B1
(45) Date of Patent: Apr. 3, 2012

(54) RESOLUTION OF 1-(4-METHOXYBENZYL)-OCTAHYDRO-ISOQUINOLINE

(75) Inventors: Murali Krishna Prasad Divi, Hyderabad (IN); Srinivas Rao Pendyala, Hyderabad (IN); Lavu Venkata Ramana, Hyderabad (IN)

(73) Assignee: Divi's Laboratories, Ltd., Hyderabad (IN)

( * ) Notice: Subject to any disclaimer, the term of this patent is extended or adjusted under 35 U.S.C. 154(b) by 0 days.

(21) Appl. No.: 13/045,987

(22) Filed: Mar. 11, 2011

(30) Foreign Application Priority Data

Jan. 18, 2011 (IN) .............................. 161/CHE/2011

(51) Int. Cl.
*C07D 471/00* (2006.01)

(52) U.S. Cl. ........................................................ 546/43

(58) Field of Classification Search ........................ None
See application file for complete search history.

(56) References Cited

U.S. PATENT DOCUMENTS

| | | | |
|---|---|---|---|
| 2,634,272 A | 4/1953 | Hellerbach et al. | |
| 2,676,177 A | 4/1954 | Schnider et al. | |
| 3,682,925 A | 8/1972 | Den Hollander et al. | |
| 4,247,697 A | 1/1981 | Mohacsi | |
| 4,556,712 A | 12/1985 | Rice | |
| 4,727,147 A | 2/1988 | Wintermeyer et al. | |
| 6,670,476 B2 * | 12/2003 | Harms | 544/349 |
| 2007/0270487 A1 | 11/2007 | Hedberg Esq. | |

FOREIGN PATENT DOCUMENTS

WO    WO 2009106547 A1 *    9/2009

OTHER PUBLICATIONS

English translation of Hungarian Patent No. 170,924.

\* cited by examiner

*Primary Examiner* — Janet Andres
*Assistant Examiner* — Timothy R Rozof
(74) *Attorney, Agent, or Firm* — Caesar, Rivise, Bernstein, Cohen & Pokotilow, Ltd.

(57) ABSTRACT

The resolution of racemic 1-(4-methoxybenzyl)-octahydro-isoquinoline, a key intermediate in the synthesis of the antitussive agent dextromethorphan, is reported using (R)-2-(6-methoxy-2-naphthyl) propionic acid in good yields. The resolving agent and the undesired isomer of the octahydro-isoquinoline have been recovered in good yield.

18 Claims, No Drawings

RESOLUTION OF 1-(4-METHOXYBENZYL)-OCTAHYDRO-ISOQUINOLINE

CROSS-REFERENCE TO RELATED APPLICATIONS

This application claims priority from India Application Serial No. 161/CHE/2011, filed on Jan. 18, 2011, entitled RESOLUTION OF 1-(4-METHOXYBENZYL)-OCTAHY-DRO-ISOQUINOINE, which application is assigned to the same assignee as this application and whose disclosure is incorporated by reference herein.

FIELD OF INVENTION

This invention relates to the resolution of 1-(4-methoxybenzyl)-octahydro-isoquinoline.

INTRODUCTION

Many analogues of morphine have been prepared and tested for various activities, particularly with a view to achieve separation of the several activities of morphine and enhance or suppress selected activities. In this regard, Hellerbach and Schnider group's contribution in developing morphinans as useful antitussives and antirheumatic analgesics should be considered as outstanding (Series of publications in Helv.Chim.Acta., between 1949 and 1962). In particular, 3-oxy-N-alkyl morphinans have acquired a prominent place in medicine. The morphinans are prepared from isoquinoline type of starting materials by cyclization. Initially they prepared the racemic forms of 3-oxy-N-alkyl morphinans, which were useful as such. However, it was quickly established that the levo and dextro isomers differed in their actions qualitatively and quantitatively. In particular, the dextro isomer of 3-methoxy-N-methyl morphinan, now commonly known as dextromethorphan, has stood the test of time as an effective and safe antitussive drug for over half a century. So, methods for preparing the dextromethorphan became necessary on a commercial scale. Schnider even predicted in one of his early publications that there is likely to be a differential demand for the dextromethorphan and its isomer levomethorphan, which proved to be remarkably true as the levomethorphan has very limited utility and has been superseded by other drugs whereas dextromethorphan enjoys a substantial reputation even today.

Schnider and Gruessner of Hoffmann la Roche (U.S. Pat. No. 2,676,177 and Helv. Chim. Acta., 34, 1951, 2211-2217) outlined processes for the resolution of 3-hydroxy and 3-methoxy-N-methylmorphinans with D-tartaric acid, but not of the base without N-substitution. They were also unable to racemise the levoisomer by-product for recycling.

BACKGROUND OF THE INVENTION:

Oxymorphinans are prepared by cyclization of 1-benzl-1,2,3,4,5,6,7,8-octahydro-isoquinoline derivatives. For convenience these 1-benzl-1,2,3,4,5,6,7,8-octahydro-isoquinoline derivatives will be referred as 'octabase' henceforth. The aryl group may be substituted with the appropriate desired substituent required in the final morphinan molecule. In dextromethorphan, the substituent is 4-methoxy, which may also be generated by methylation later if a hydroxy substituent is used instead of the methoxy. The nitrogen atom of the octahydro-isoquinoline may be free base or substituted with alkyl or aralkyl groups. Here also, the option exists of N-methylation before cyclization or after cyclization. Hellerbach et al. have demonstrated that these substituents influence the outcome of cyclization in terms of yield and purity (Helv.Chim.Acta., 39, 1956, 429-440). When 1-(4-methoxybenzyl)-2-methyl-1,2,3,4,5,6,7,8-octahydroisoquinoline is cyclized, a mixture of levo and dextro isomers of methorphan is obtained. The isomers can be separated fairly easily by using resolving agents like tartaric acid, mandelic acid etc. However, only about 40% of the racemic mixture is recovered in usable form, the remaining material being of little value (Schnider and Gruessner, Helv. Chim. Acta., 34, 1951, 2211-2217). Some efforts were made to racemize the unwanted residual mixture with no success. Because of the rigid stereochemistry of the morphinan, it was expected not to undergo racemization. Mohacsi, E., has described methods of preparing 3-phenoxy-morphinans, which are obtained as racemic compounds. In passing, he mentions that the racemates can be resolved "to levorotatory compounds by any conventional method of optical resolution with acid resolving agents like tartaric acid, mandelic acid, camphor sulfonic acid, dibenzoyl tartaric acid, gulonic acid". No examples for the resolution are given (U.S. Pat. No. 4,247,697).

It was also noted during the cyclization experiments that the stereochemistry of the resulting morphinan is dependent on the enantiomeric property of the octabase used. Because the morphinan structure is a fused ring system involving the chiral centres at the ring junctions, the structure is rigid and the chirality of the octabase determines the stereochemistry of the resulting morphinan. Thus the levorotatory octabase yields dextrorotatory morphinan and vice versa (Schnider et al, Helv.Chim.Acta., 37, 1954, 710-720). It is thus advantageous to use (−) octabase for cyclization to obtain (+) morphinan. This is possible only if there is an economically viable process for making the required chiral octabase, which is possible to achieve by either ways: (1) to resolve the racemic mixture of the octabase, use the right isomer in further cyclization process, recover and recycle the unwanted isomer or (2) prepare the required isomer of the octabase by a stereospecific synthesis. There are indeed numerous publications and patents targeting the latter approach, some being effective. However, the major drawback in all these processes are the expensive and sophisticated metal catalysts, ligands and reaction conditions required. Traditionally the resolution methods are simple, using easily available chiral resolving agents. The success of a resolution process depends on the efficiency of resolution step in separating the two isomers, yield and recovery of the desired isomer of high purity, recovery and recyclability of the resolving agent and the undesired isomer.

Schnider et al. (Helv. Chim. Acta., 37, 1954, 710-720) resolved racemic 1-(4-methoxybenzyl)-N-methyl octahydroisoquinoline with D-tartaric acid as tartrate and after recrystallisation converted to the required octabase. The tartrate salt of the undesired octabase remained in solution and recovered in low yield as tartrate and further work up gave the corresponding octabase in low yield. Our own efforts to resolve the octabase with L-(+) tartaric acid were entirely unsuccessful. In a later publication, Brossi and Schnider (Helv. Chim. Acta., 39, 1956, 1376-1386) reported resolution of the same racemic octabase with mandelic acid without details of yield or quality of the recovered octabase or recovery of the undesired isomer. In Table 1 below our results obtained using mandelic acid as a resolving agent as described in the above literature and with minor modifications are summarized.

TABLE 1

Resolution with (−) Mandelic acid

| Expt. | OR of input mandelic acid | Solvent | Yield (%) of salt | OR of Salt | OR of recovered resolving agent from salt | from MLs |
|---|---|---|---|---|---|---|
| 1 | −150° to −152° | Ethyl acetate & Methanol | 37 | −126° to −132° | −150° to −152° | −135° to −140° |
| 2 | −150° to −152° | Ethyl acetate | 38 | −120° to −125° | −150° to −152° | −135° to −140° |
| 3 | −150° to −152° | Toluene | — | — | — | — |
| 4 | −150° to −152° | Methanol | — | — | — | — |

The results show that only a mixture of solvents is able to resolve the octabase satisfactorily. Without ethyl acetate, and in single solvents, the salt does not seem to form. On an industrial scale, single solvents are preferred to achieve good recovery and recycle.

Hollander et al. have described resolution of racemic octabase with di-isopropylidene-1-ketogulonic acid, an intermediate in the synthesis of ascorbic acid from glucose, including recovery of the resolving agent and the undesired isomer (U.S. Pat. No. 3,682,925 and U.S. Pat. No. 3,955,227). However, no yields or method of recycling of either are given. The salt formation requires seeding, elevated temperature and long hours of agitation. The authors also have described resolution of the 3-hydroxy-N-methylmorphinan and 3-methoxymorphinan with the same resolving agent but with no details of recovery of the resolving agent or the undesired isomer or how these are utilized later.

Wintermeyer et al. (U.S. Pat. No. 4727147) have described another method of resolving the isomers of 1-(4-methoxybenzyl)-octahydroisoquinoline by conversion to its acetate and spontaneous crystallization from a saturated solution by seeding with the required isomer. Their results show a good recovery of both the isomers as fairly optically pure products. The advantage is that no chiral resolving agent is used. However the process requires several recrystallisations to achieve satisfactory yields and purity. Another drawback is that there is no indication of how the undesired isomer is to be recycled or whether the purity of the desired isomer so obtained is adequate for further synthesis.

Gentile, A, et al. have reported the resolution of tetrahydropapaverine and related isoquinolines using several commercially available NSAIDs like (S)-ibuprofen, (S)-flurbiprofen, (S)-naproxen (IT2008MI319=WO2008EP52234). Hedberg et al. have listed (R)- and (S)-naproxen as resolving agents along with a number of other chiral organic acids for phenylpropanolamines, although no examples are given using these agents for resolution (U.S.20070270487). Only mandelic acid and its derivatives are actually reported in the resolution examples in this now abandoned application.

Thus, there is need for an efficient process for resolution of the racemic O-methyl octabase without N-substitution and recovery of both the isomers in good yield besides recovery and recycling of the resolving agent. To achieve commercial viability of the process, it is also imperative to regenerate the required isomer from the unwanted isomer so recovered.

Just as there are no reports of racemization of the undesired isomer of 3-oxymorphinans, there are also no reports of direct racemization of the undesired (+) octabase in the literature. Conversion of the recovered undesired isomer of the octabase to the required isomer before its cyclization to the required dextro-isomer of the morphinan thus involves chemical transformations. Schnider et al. (Helv. Chim. Acta., 37, 1954, 710-720) achieved a chemical transformation of the isomer partially by first oxidizing to N-oxide, reduction to hydroxylamine compound, cleaving of the isoquinoline ring and finally re-cyclization to racemic octabase. Obviously, the whole process proved cumbersome and uneconomic. Due to low recovery of the undesired isomeric octabase and the cumbersome recyclisation process, the scheme was never adopted commercially. Brossi and Schnider (Helv. Chim. Acta., 39, 1956, 1376-1386) designed a method of dehydrogenating the optically active octabases (both 4-hydroxy and 4- methoxybenzyl analogs with unsubstituted N-atom) to corresponding 5,6,7,8-tetrahydro- isoquinolines followed by quaternisation of the nitrogen atom with benzylbromide, hydrogenation of the isoquinoline ring with catalysts Raney-nickel in 1-methylnaphthalene or palladium-carbon in tetralin and finally debenzylation of the nitrogen atom resulting in racemic octabase. They also succeeded in direct reduction of the tetrahydro-isoquinoline with sodium and amyl alcohol with yields of 15 to 40%. Still, the whole process could not be commercially adopted. However, for this purpose they obtained the required octabases without N- substitution, from the hexabase, 1-(4-methoxybenzyl)-3,4,5,6,7,8-hexahydro-isoquinoline, by reduction with Raney-nickel which in its turn was obtained by cyclization of the amide precursor (Schnider and Hellerbach, Helv. Chim. Acta., 33, 1950, 1437). Thus, they have not reported direct racemization or resolution of the 0-methyl octabases without N-substitution.

Szanta Csala et al. (HU 170924) have reported a novel method of racemization of the unwanted isomer by treatment with sodium hypochlorite or N-chlorobenzenesulfonamide or t-butylhypochlorite followed by reduction with sodium borohydride or hydrogenation in the presence of catalysts like Raney-nickel or palladium-carbon. The yields reported are between 50 and 65%. According to them, the octabase undergoes N-chlorination and dehydrochlorination in the presence of base to yield a corresponding C=N bond, which is then reduced (hydrogenated) with the borohydride. In this process, it is necessary that the nitrogen atom is not substituted. Kenner (U.S. Pat. No. 4,556,712) has described a similar method of conversion of unwanted optically active 1-(alkoxybenzyl)-1,2,3,4-tetrahydro-isoquinoline to corresponding 3,4-dihydro-isoquinoline by oxidation (selective dehydrogenation) with hypohalites followed by hydrogenation with sodium borohydride or sodium hydride to corresponding racemic 1,2,3,4-tetrahydro-isoquinoline. The reported yields are about 54% at the final reduction stage. However they have not reported similar efforts with octabase analogs.

An effective resolution of the 0-methyl racemic octabase without N-substitution is an objective of the present invention. By effective resolution it is understood to mean to one skilled in the art a commercially viable recovery of the required (−) octabase, good recovery of the resolving agent fit for recycling and a good recovery of the unwanted (+) octabase such that it can be recycled suitably.

It is also an objective of the process of the present invention to demonstrate a satisfactory recycling of the unwanted (+) octabase so recovered for value addition.

SUMMARY OF THE INVENTION:

It has been possible to achieve a very good resolution of the racemic 1-(4-methoxybenzyl)-octahydroisoquinoline (racemic octabase or DL octabase) with the unusual resolving agent (R)-2-(6-methoxy-2-naphthyl)-propionic acid (henceforth simply referred to as R-naproxen). It has also been possible to recover the resolving agent in a quality fit for recycling as a resolving agent. It has also been possible to recover the unwanted (+) octabase, satisfactory both in quality and quantity, for regenerating the racemic octabase for recycling in the resolution step.

DETAILED DESCRIPTION OF THE INVENTION:

The required racemic octabase, 1-(4-methoxybenzyl)-1,2,3,4,5,6,7,8-octahydro-isoquinoline, was prepared by Bischler-Napieralski cyclization of the amide formed by condensing 2-(1-cyclohexenyl)-ethylamine and 4-methoxyphenylacetic acid as described by Hellerbach in U.S. Pat. No. 2,634,272 with some minor modifications. It is generally convenient and expedient to use the octabase in the organic layer as obtained after the reaction is completed without isolation or further purification. However, it is possible to isolate the octabase and use as a crude or purified material. The octabase is sensitive to light and air. If desired, the isolated octabase may be converted to a stable salt such as hydrobromide or hydrochloride and stored to be used later. In such a process, it would become necessary to liberate the free base before the resolution step is undertaken. Although toluene is the preferred solvent, other solvents may be used. These points are illustrated in Table 2 below.

The resolving agent, R-naproxen, as usually obtained, is not chirally pure and needs to be purified further to obtain an optical rotation of −60° and more. Surprisingly, it was found that a high chiral purity is not necessary for an effective resolution of the octabase. An optical rotation of −40° for the R-naproxen was found to be adequate to effect good resolution. Table 2 below shows the typical results of resolution with different grades of R-naproxen. Unexpectedly, the contaminating S-naproxen in the low purity R-naproxen does not interfere with the resolution process. A welcome benefit from this is the lower cost of less pure R-naproxen, i.e., the cost of purification of the resolving agent is saved.

TABLE 2

Resolution of Octabase with R-Naproxen

| Expt. | OR of input naproxen | Solvent | Yield (%) of salt | OR of Salt | OR of recovered resolving agent from salt | from MLs |
|---|---|---|---|---|---|---|
| 1 | −40° | Toluene | 33.8 | −70° to −75° | −50° to −52° | −30° to −32° |
| 2 | −50° | Toluene | 34 | −70° to −75° | −52° to −55° | −47° to −50° |
| 3 | −60° | Toluene | 36 | −70° to −75° | −62° to 65° | −58° to −58° |
| 4 | −40° | Ethyl acetate | 33.8 | −70° to −75° | −50° to −52° | −30° to −32° |
| 5[a] | −40° | Toluene | 34.5 | −70° to −75° | −50° to −52° | −30° to −32° |
| 6[b] | −40° | Toluene | 33.8 | −70° to −75° | −50° to −52° | −30° to −32° |

[a]Octabase liberated in situ from solid hydrobromide salt just before resolution
[b]Octabase treated with R-naproxen in toluene

EXAMPLES

The resolving agent R-naproxen is routinely recovered as a by product during the resolution of racemic naproxen produced in ton quantities at Divis laboratories and is easily available to us.

The following examples are intended to be illustrative of the process and are not limiting. A competent person skilled in the art may be able to modify details to suit the specific needs.

Example 1

Resolution of (+)-1-(4-methoxybenzyl)-1,2,3,4,5,6,7,8-octahydro-isoquinoline

To a solution of racemic octabase (50.0 g, 0.1942 moles) in 300 ml of toluene, solid R-naproxen (36.4 g, 0.157 moles) is added. The reaction mixture is warmed to 45-55° C. and then stirred for 1 h at the same temperature. The mass is allowed to cool to 25-35° C., maintained for about 30 minutes, further cooled to 6-14° C. and aged for 2 h at the same temperature. The (−) octabase-R-naproxen salt thus formed is filtered at 6-14° C. and the wet cake is washed with 30 ml of toluene. It is then purified by making a slurry in toluene, maintaining at 40-50° C. for about 1 h, cooled to 25-35° C., then further cooled to 6-14° C., stirred for 2 h, filtered, washed with toluene (4.5 ml) and dried to yield the crystalline (−) octabase-R-naproxen salt (32.0 g, 33.8% yield) of optical rotation: (−) 70 to 75° in 1% methanol at 20° C., 589 nm. The mother liquors containing the undesired enantiomer (+octabase) are reserved for recovery and racemization.

Example 2

Resolution of (±)-1-(4-methoxybenzyl)-1,2,3,4,5,6,7,8-octahydro-isoquinoline

Racemic octabase HBr salt (131.5 g) is taken in a flask with 500 ml water, cooled to 10-15° C., the pH is adjusted to 12 to 13 with caustic soda lye and 325 ml of toluene is charged to extract the liberated free racemic octabase. The toluene layer is washed with water and the organic layer is dried. The toluene layer containing 100.0 g (0.388 moles) of free octabase is charged into a flask and 200 ml toluene is added. To this solution, solid R-naproxen (72.8 g, 0.316 moles, optical rotation about −40° is added. The reaction mixture is warmed to 45-55° C., stirred for 1 h, then cooled to 25-35° C., maintained for about 30 minutes, further cooled to 6-14° C. and maintained for 2 h at the same temperature. The (−) octabase-R-naproxen salt thus formed is filtered at 6-14° C. and the wet cake is washed with 60 ml of toluene. The mother liquors are collected separately for recovery of R-naproxen, DL-octabase and (+)-octabase.

The (−) octabase-naproxen salt is purified by making a slurry in toluene at 45-55° C. for about 1 h then cooled to 25 to 35° C., further cooled to 6-14° C., stirred for 2 h, filtered, washed with toluene (9 ml) and dried to yield the crystalline (−) octabase-R-naproxen salt (65.0 g, 34.5% yield) optical rotation: (−) 70 to 75° in 1% MeOH at 20° C., 589 nm; HPLC:>99%.

Example 3

Resolution of (±)-1-(4-methoxybenzyl)-1,2,3,4,5,6,7,8-octahydro-isoquinoline

The toluene layer containing about 100 g (0.388 moles) of the racemic octabase as in example 2 above is concentrated under vacuum at below 50° C. to remove toluene to obtain crude racemic octabase mass. To this, sufficient ethyl acetate is charged to make up the total volume to 400 ml. To this solution solid R-naproxen (72.8 g, 0.316 moles, optical rotation is about −40°) is added. The reaction mixture is warmed to 45-55° C., stirred for 1 h, then cooled to 25-35° C., maintained for about 30 minutes, further cooled to 6-14° C. and maintained for 2 h at the same temperature. The (−) octabase-R-naproxen salt thus formed is filtered at 6-14° C. and the wet cake is washed with 60 ml of ethyl acetate. The mother liquors are collected separately for recovery of R-naproxen, DL-octabase and (+) octabase.

The (−) octabase-naproxen salt is purified by making a slurry in ethyl acetate at 45-55° C. for about 1 h then cooled to 25-35° C., further cooled to 6-14° C., stirred for 2 h, then filtered and washed with ethyl acetate (9 ml) and finally dried to yield crystalline (−) octabase-R-naproxen salt. (64 g, 33.78% yield). Optical rotation: (−) 70 to 75° in 1% MeOH at 20° C., 589 nm; HPLC:>99%.

Example 4

Resolution of (±) 1-(4-Methoxybenzyl)-octahydro-isoquinoline with recovered R-Naproxen About 1100 kg of racemic octabase in about 6500 L of toluene is charged into a reactor under nitrogen atmosphere. R-Naproxen recovered from decomposition of the (−) octabase-R-naproxen salt or from the mother liquors from the process at earlier steps separately or suitably blended to exhibit an optical rotation of not less than (−) 40°, is taken in toluene as a suspension and charged into the reactor, the temperature raised to 50±5° C. and maintained for about one hour. The material is cooled to 30±5° C., maintained for about of 30 minutes, further cooled to 6-14° C. and maintained for another 2 h. The (−) octabase-R-naproxen salt thus formed is filtered/centrifuged at 6-14° C. and washed with toluene. It is then charged into another reactor, 1500 L toluene charged and warmed to 40-50° C., maintained for about 1 h, cooled to 25-35° C., further cooled to 6-14° C., stirred for 2 h, filtered, washed with toluene and dried to yield the crystalline (−) octabase-R-naproxen salt (about 704 Kg, 33.78% yield) of optical rotation: (−) 70 to 75° in 1% methanol at 20° C., 589 nm. The mother liquors are collected separately for recovery of R-Naproxen, DL-Octabase and (+) Octabase.

Example 5

Liberation of (−) Octabase from its R-naproxen Salt

The (−) octabase-R-naproxen salt (64 g) is taken in a flask with 300 ml of water and 600 ml toluene. The contents are cooled to 10-15° C. The pH is adjusted to 10 to 13 with caustic soda lye. Phases are separated, and the aqueous phase containing the R-naproxen sodium salt is taken up for R-naproxen recovery. The organic phase containing the (−) octabase is washed with demineralised water and dried. The organic phase is concentrated under vacuum below 40° C. to remove toluene. The isolated (−) octabase weight: 33.5 g (yield about 99% from (−) octabase-R-naproxen salt); optical rotation: (−) 145 ° to (−) 150° [C=1% methanol, 20° C., 589 nm]; HPLC:>99%. The (−) octabase so obtained is used in the dextromethorphan synthesis. Alternatively, the (−) Octabase base present in the organic phase can be used as such in the dextromethorphan synthesis.

Example 6

Recovery of Naproxen from the Aqueous Layer of (−) Octabase Liberation Step

The aqueous layer containing the R-naproxen sodium salt from the above (−) octabase liberation step is taken up in a flask, cooled to 10-15° C., the pH is adjusted to <2 with HCl (about 45 ml) and about 180 ml toluene is charged into the flask. The contents are heated to about 80° C. and the phases are separated. The aqueous phase is discarded and the organic phase is washed with about 100 ml of water, then cooled to 10-15° C. and maintained for about 1 h at the same temperature. The precipitated R-naproxen is filtered and washed with 10 ml of toluene. The wet cake is dried under vacuum at 60-70° C. until constant weight. Yield: 30.2 g (more than 99% from the (−) octabase-R-naproxen salt used); Optical rotation: (−) 50 to (−) 52° (C=1% in methanol, 25° C., 589 nm); HPLC:>98%. Alternatively, the R-naproxen present in the toluene layer can be used as such, after partial concentration without isolation, after the resolution step.

Example 7

Recovery of R-Naproxen, DL-Octabase and (+) Octabase from Mother Liquors (a) Recovery of R-Naproxen: The mother liquor obtained from input of 100 g of racemic octabase in the resolution step is taken in a flask and about 285 ml water added. The mixture is cooled to <20° C., pH adjusted to 11-13 with about 15 ml of caustic soda lye and the phases are separated. The organic phase is reserved for recovery of DL-octabase. The aqueous layer containing the R-naproxen sodium salt is taken up in a flask, cooled to 10-15° C., the pH adjusted to <2 with HCl and about 385 ml toluene is charged into the flask. The contents are heated to about 80° C. and the phases are separated. The aqueous phase is discarded, the organic phase washed with about 100 ml of water, then cooled to 10 to 15° C. and maintained for about 1 h at the same temperature. The R-naproxen is filtered and the wet cake is washed with 10 ml of toluene. The wet cake is dried under the vacuum at 60-70° C. until constant weight. Yield: 39 g; Optical rotation: (−) 30° to (−) 32° (C=1% in methanol, 25° C., 589 nm); HPLC: >98%. Alternatively the R-naproxen present in the toluene layer can be used as such after partial concentration without isolation. The organic phase is taken up for recovery of DL-octabase.

(b) Recovery of DL-Octabase:

The organic phase obtained in step (a) above contains predominantly (+) octabase, some unresolved racemic octabase and some non-basic impurities. It is charged with about 300 ml of water and about 45 ml of HCl and stirred for about 30 minutes at 35° C. The phases are separated and the waste organic phase containing the non-basic impurities is taken up for solvent recovery.

The aqueous phase (containing the octabase as HCl salt) is cooled to 10-15° C. and pH adjusted to 10-13 with about 28 ml caustic soda lye. The free base thus liberated is extracted into about 70 ml toluene. The phases are separated, the aqueous phase discarded and the organic phase is washed with water.

The organic phase containing predominantly (+) octabase and some unresolved racemic octabase is taken in a flask, cooled to 20° C. and then about 6 g anhydrous formic acid is added. The contents are stirred for about 4 h at 20° C. and the racemic octabase formate salt is filtered and the wet cake is washed with about 10 ml toluene. The mother liquors are used to recover the (+) octabase.

The wet cake is taken up to liberate free base by the usual procedure using caustic soda lye and water. The liberated free base is extracted into 50 ml toluene. The phases are separated, the aqueous phase discarded, the organic phase washed with water and checked for chemical assay before it is used in the resolution step. Active octabase yield: about 20 g; Optical rotation of the concentrated crude: 0° to (+) 10 ° (C=1% in methanol, 20° C., 589 nm); HPLC:>99%.

(c) Recovery of (+) Octabase from the Mother Liquors:

The toluene mother liquors, after isolation of the formate salt as in step (b) above, containing predominantly (+) octabase and traces of racemic octabase, are charged into a flask, 61 ml of water are added and basified to pH 10 to 12 with caustic soda lye. The phases are separated, the aqueous phase is discarded and the organic phase is washed with water. The organic layer thus obtained is subjected to a racemization step after estimating the octabase assay by titration. Active octabase yield: about 35 g; Optical rotation of the concentrated crude: (+) 125° to (+) 135° (C=1% in methanol, 20° C., 589 nm); HPLC:>95%.

Example 8

Racemization of (+) Octabase

This is achieved as per the method described by Szanta Csala et al. (HU 170924) with some modifications.

A solution of 100 g of (+) octabase obtained from any of the above procedures in toluene is treated with dilute acetic acid and cooled to -3±3° C. A solution of sodium hypochlorite (hypo) is added and the reaction mixture is maintained at a low temperature until the absence of the octabase by TLC test. The phases are separated, aqueous layer discarded and the organic layer washed with water and dried with sodium sulphate. To the cooled organic layer, a solution of methanolic NaOH is added, the mixture warmed and stirred for some time. The reaction progress is checked by TLC for the absence of chlorobase. After the reaction is completed, the reaction mass containing the hexabase is diluted with water and a solution of sodium borohydride is slowly added. The progress of the reaction is monitored by TLC for the absence of hexabase. The reaction mixture is further diluted with water, phases separated, aqueous layer discarded and the organic layer washed with water. The octabase content in the organic phase is estimated by titration. Yield: About 60 g (60%) in toluene solution. The toluene solution containing racemic octabase obtained as above is recycled in a resolution step.

We claim:

1. A process for resolution of racemic 1-(4-methoxybenzyl)-1,2,3,4,5,6,7,8-octahydroisoquinoline with R-naproxen comprising:
   (a) treating a solution of the racemic octabase 1-(4-methoxybenzyl)-2-methyl-1,2,3,4,5,6,7,8-octahydroisoquinoline in a suitable solvent with solid R-naproxen or a solution thereof in a suitable solvent,
   (b) collecting the crystallized salt of (−) 1-(4-methoxybenzyl)-1,2,3,4,5,6,7,8-octahydroisoquinoline with R-naproxen, optionally purifying it by recrystallisation and reserving the mother liquors for recovery of unreacted racemic 1-(4-methoxybenzyl)-1,2,3,4,5,6,7,8-octahydroisoquinoline, (+) 1-(4-methoxybenzyl)-1,2,3,4,5,6,7,8-octahydroisoquinoline and excess of R-naproxen, if any,
   (c) decomposing the salt as obtained in step (b) above with an alkaline reagent, in the presence of an immiscible organic solvent in which the liberated (−) 1-(4-methoxybenzyl)-1,2,3,4,5,6,7,8-octahydroisoquinoline is soluble, separating the liquid mixture into aqueous and organic solvent phases, reserving the aqueous phase for recovery of R-naproxen; and
   (d) recovering the free (−) 1-(4-methoxybenzyl)-1,2,3,4,5,6,7,8-octahydroisoquinoline from the organic solvent phase as obtained in step (c) above by removing the solvent, or optionally using the organic solvent phase directly to synthesize dextromethorphan.

2. The process as in claim 1 wherein the R-naproxen has an optical rotation of (−) 40° to (−) 60°.

3. The process as in claim 1 wherein the R-naproxen is in a mole ratio of 0.5 to 1.0 moles with respect to the racemic 1-(4-methoxybenzyl)-1,2,3,4,5,6,7,8-octahydroisoquinoline.

4. The process as in claim 1 (a) wherein for the racemic 1-(4-methoxybenzyl)-1,2,3,4,5,6,7,8-octahydroisoquinoline and R-naproxen the solvent is toluene or ethyl acetate.

5. The process as in claim 1 (c) wherein the organic solvent is toluene or ethyl acetate.

6. The process as in claim 1 (b) wherein the mother liquor (i) is treated with caustic soda lye to convert the R-naproxen to its sodium salt, (ii) the organic phase is separated from the aqueous phase containing the R-naproxen sodium salt, (iii) the aqueous phase is acidified with aqueous hydrochloric acid to precipitate free R-naproxen, (iv) the R-naproxen from the mixture is extracted with toluene or ethyl acetate, and (v) the solvent is removed to recover solid R-naproxen fit for recycling as a resolving agent in another batch.

7. The process as in claim 1 (c) wherein the aqueous phase is (i) acidified with hydrochloric acid to precipitate free R-naproxen, (ii) the R-naproxen is a extracted from the mixture with toluene or ethyl acetate and (iii) the solvent is removed to recover solid R-naproxen is fit for recycling as a resolving agent in another batch.

8. The process as in claims 1(b) and 6 wherein the organic phase obtained in claim 6(ii) is treated with formic acid, the racemic 1-(4-methoxybenzyl)-1,2,3,4,5,6,7,8-octahydroisoquinoline formate salt formed is filtered off and the mother liquor containing (+) 1-(4-methoxybenzyl)-1,2,3,4,5,6,7,8-octahydroisoquinoline utilized for recovery and racemization of the (+) 1-(4-methoxybenzyl)-1,2,3,4,5,6,7,8-octahydroisoquinoline for recycling in the resolution step.

9. The process as in claim 8 wherein the formate salt obtained is further converted to free racemic 1-(4-methoxybenzyl)-1,2,3,4,5,6,7,8-octahydroisoquinoline for recycling in a resolution step.

10. A process for resolution of racemic 1-(4-hydroxybenzyl)-1,2,3,4,5,6,7,8-octahydro-isoquinoline with R-naproxen comprising:
   (a) treating a solution of the racemic 1-(4-hydroxybenzyl)-1,2,3,4,5,6,7,8-octahydro-isoquinoline in a suitable solvent with solid R-naproxen or a solution thereof in a suitable solvent,
   (b) collecting the crystallized salt of (−) 1-(4-hydroxybenzyl)-1,2,3,4,5,6,7,8-octahydro-isoquinoline with R-naproxen, optionally purifying it by recrystallisation and reserving the mother liquors for recovery of unreacted racemic 1-(4-hydroxybenzyl)-1,2,3,4,5,6,7,8-octahydro-isoquinoline, (+) 1-(4-hydroxybenzyl)-1,2,3,4,5,6,7,8-octahydro-isoquinoline and excess of R-naproxen, if any,
   (c) decomposing the salt as obtained in step (b) above with an alkaline reagent, in the presence of an immiscible organic solvent in which the liberated (−) 1-(4-hydroxybenzyl)-1,2,3,4,5,6,7,8-octahydro-isoquinoline is soluble, separating the liquid mixture into aqueous and organic solvent phases, reserving the aqueous phase for recovery of R-naproxen; and
   (d) recovering the free (−) 1-(4-hydroxybenzyl)-1,2,3,4,5,6,7,8-octahydro-isoquinoline from the organic solvent phase as obtained in step (c) above by removing the solvent, or optionally using the organic solvent phase directly to synthesize dextromethorphan.

11. The process as in claim 10 wherein the R-naproxen has an optical rotation of (−)40° to (−)60°.

12. The process as in claim 10 wherein the R-naproxen is in a mole ratio of 0.5 to 1.0 moles with respect to the racemic 1-(4-hydroxybenzyl)-1,2,3,4,5,6,7,8-octahydro-isoquinoline.

13. The process as in claim 10 (a) wherein for the racemic 1-(4-hydroxybenzyl)-1,2,3,4,5,6,7,8-octahydro-isoquinoline and R-naproxen the solvent is toluene or ethyl acetate.

14. The process as in claim 10 (c) wherein the organic solvent is toluene or ethyl acetate.

15. The process as in claim 10 (b) wherein the mother liquor (i) is treated with caustic soda lye to convert the R-naproxen to its sodium salt, (ii) the organic phase is separated from the aqueous phase containing the R-naproxen sodium salt, (iii) the aqueous phase is acidified with aqueous hydrochloric acid to precipitate free R-naproxen, (iv) the R-naproxen from the mixture is extracted with toluene or ethyl acetate, and (v) the solvent is removed to recover solid R-naproxen fit for recycling as a resolving agent in another batch.

16. The process as in claim 10 (c) wherein the aqueous phase is (i) acidified with hydrochloric acid to precipitate free R-naproxen, (ii) the R-naproxen is a extracted from the mixture with toluene or ethyl acetate and (iii) the solvent is removed to recover solid R-naproxen is fit for recycling as a resolving agent in another batch.

17. The process as in claims 10 (b) and 15 wherein the organic phase obtained in claim 6 (ii) is treated with formic acid, the racemic 1-(4-hydroxybenzyl)-1,2,3,4,5,6,7,8-octahydro-isoquinoline formate salt formed is filtered off and the mother liquor containing (+) 1-(4-hydroxybenzyl)-1,2,3,4,5,6,7,8-octahydro-isoquinoline utilized for recovery and racemization of the (+) 1-(4-hydroxybenzyl)-1,2,3,4,5,6,7,8-octahydro-isoquinoline for recycling in the resolution step.

18. The process as in claim 17 wherein the formate salt obtained is further converted to free racemic 1-(4-hydroxybenzyl)-1,2,3,4,5,6,7,8-octahydro-isoquinoline for recycling in a resolution step.

* * * * *